United States Patent
Lindsay

(10) Patent No.: US 9,643,935 B2
(45) Date of Patent: May 9, 2017

(54) PROCESS FOR PREPARING 4,6-BIS(ARYLOXY) PYRIMIDINE DERIVATIVES

(71) Applicant: CHEMINOVA A/S, Harboøre (DK)

(72) Inventor: Karl Bernhard Lindsay, Harboøre (DK)

(73) Assignee: CHEMINOVA A/S, Harboøre (DK)

(*) Notice: Subject to any disclaimer, the term of this patent is extended or adjusted under 35 U.S.C. 154(b) by 0 days.

(21) Appl. No.: 14/893,666

(22) PCT Filed: May 27, 2014

(86) PCT No.: PCT/DK2014/050145
§ 371 (c)(1),
(2) Date: Nov. 24, 2015

(87) PCT Pub. No.: WO2014/190997
PCT Pub. Date: Dec. 4, 2014

(65) Prior Publication Data
US 2016/0137612 A1    May 19, 2016

(30) Foreign Application Priority Data

May 28, 2013    (EP) .................................... 13169497

(51) Int. Cl.
*C07D 239/52*    (2006.01)

(52) U.S. Cl.
CPC .................. *C07D 239/52* (2013.01)

(58) Field of Classification Search
CPC .................................................... C07D 239/52
See application file for complete search history.

(56) References Cited

U.S. PATENT DOCUMENTS

| | | | | |
|---|---|---|---|---|
| 5,849,910 A | * | 12/1998 | Kameswaran | C07D 239/52 544/299 |
| 5,977,363 A | * | 11/1999 | Wood | C07D 239/52 544/216 |
| 6,087,498 A | * | 7/2000 | Wood | C07D 239/52 544/299 |
| 6,153,750 A | | 11/2000 | Whitton et al. | |
| 6,734,304 B2 | | 5/2004 | Weintritt et al. | |
| 2010/0063275 A1 | | 3/2010 | Beveridge et al. | |
| 2010/0179320 A1 | | 7/2010 | Liu et al. | |

FOREIGN PATENT DOCUMENTS

| | | |
|---|---|---|
| EP | 242081 A1 | 10/1987 |
| GB | 2291874 A | 2/1996 |
| WO | WO-92/08703 A1 | 5/1992 |
| WO | WO-98/07707 A1 | 2/1998 |
| WO | WO-98/18767 A1 | 5/1998 |
| WO | WO-01/72719 A1 | 10/2001 |
| WO | WO-2006/114572 A2 | 11/2006 |
| WO | WO-2008/043977 A1 | 4/2008 |
| WO | WO-2008/075341 A1 | 6/2008 |

OTHER PUBLICATIONS

Schwesinger, Reinhard, et al., Extremely Strong, Uncharged Auxilliary Bases; Monomeric and Polymer-Supported Polyaminophosphazenes (P2-P5), Liebigs Ann. 1996, 1055-1081.
International Search Report for PCT/DK2014/050145, ISA/EP, Rijswijk, NL, mailed Jul. 25, 2014.

* cited by examiner

*Primary Examiner* — Golam M M Shameem
(74) *Attorney, Agent, or Firm* — Harness, Dickey & Pierce, P.L.C.

(57) ABSTRACT

Process for preparing 4,6-bis(aryloxy)pyrimidine derivatives. A process is provided for preparing 4,6-bis(aryloxy)pyrimidine derivatives. The process is conducted in water as reaction medium and catalyzed by one or more tertiary-amine catalyst(s). It has been found that a water based reaction substantially free of organic solvents can be carried out providing excellent yields by the addition of one or more tertiary-amine catalysts to the reaction medium. This provides a clean reaction and produces the desired product in high yields.

20 Claims, No Drawings

PROCESS FOR PREPARING 4,6-BIS (ARYLOXY) PYRIMIDINE DERIVATIVES

CROSS-REFERENCE TO RELATED APPLICATIONS

This application is a 371 U.S. National Stage of International Application No. PCT/DK2014/050145, filed May 27, 2014, which claims the benefit of and priority to European Patent Application No. 13169497.8, filed May 28, 2013. The entire disclosures of the above applications are incorporated herein by reference.

The present invention relates to a novel process for producing 4,6-bis(aryloxy)pyrimidines derivatives. The process is conducted in water as reaction medium and catalyzed by one or more tertiary-amine catalyst(s). Using one or more tertiary-amine catalyst(s) in combination with water as reaction medium makes the process more desirable than known production methods as it is more environmental friendly and reduces the production costs.

BACKGROUND

A method for preparation of the fungicidal active compound Azoxystrobin is described in International patent publication no. WO 98/18767 wherein water is used as the only reaction medium. However, the process provides relatively low yields and requires long reaction time. To increase the yield potassium fluoride is added to the reaction mixture but potassium fluoride is highly toxic and corrosive to metals and therefore undesirable for large scale application. As seen from the results provided for in WO 98/18767 high production yields of azoxystrobin without using potassium fluoride are only obtainable by substituting water as reaction medium with an organic solvent such as toluene. On laboratory scale, high yields of azoxystrobin have also been provided when conducting the reaction as a melt i.e. without reaction medium. However, this procedure is non-advantageous at large production scale due to both difficulties in stirring of the melt, but also difficult to solubilize the organic compounds i.e. starting materials and products during purification which results in low yields.

The use of 1,4-diazabicyclo[2.2.2]octane (referred to as DABCO) as a catalyst in the preparation of asymmetrical 4,6-bis(aryloxy)pyrimidine derivatives is disclosed in International patent publication no. WO 2001/72719. Use of DABCO as a catalyst enhances the yield and reduces the reaction time. The process is stated to be carried out in an organic solvent. However, the process may also be conducted in an aqueous two-phase system in which it is said to be advantageous to remove the water again during the reaction. Suitable co-solvents for use in such an aqueous two-phase system are said to be solvents which are at least partially water immiscible.

Using a low catalytic loading of DABCO is described in International patent publication no. WO 2006/114572 when producing asymmetrical 4,6-bis(aryloxy)pyrimidine derivatives. The process is preferably carried out in an organic solvent. Again it is stated that the process may also be conducted in an aqueous two-phase system in which it is advantageous to remove the water during the reaction. Suitable co-solvents for use in such an aqueous two-phase system are solvents which are at least partially water immiscible.

Quinuclidine-based or 3-substituted N-methyl pyrrolidine based compounds has been described in International patent publication no. WO 2008/043977 as successful catalysts used in producing asymmetrical 4,6-bis(aryloxy)pyrimidine derivatives. The process described is preferably carried out in an organic solvent, but the process may also be conducted in an aqueous two-phase system in which it is advantageous to remove the water during the reaction. Suitable co-solvents for use in such an aqueous two-phase system are solvents which are at least partially water immiscible.

An alternative method for producing azoxystrobin is described in International patent publication no. WO 2008/075341. The process comprises a 4-step process in which the first step comprise reacting a phenol-derivative with a base in an organic solvent to obtain a phenolate salt, wherein water is removed from the reaction mixture during the reaction. The second and third step comprises adding the aromatic substrate to the reaction mixture and thereby applying heat to the mixture. The final and fourth step, comprise removal of the solvent and isolating and purifying the substrate.

In United States patent application published as US 2010/0179320-A1 yet another alternative process is disclosed for the manufacture of azoxystrobin. This process involves a formylation step of an azoxystrobin intermediate in the presence of a Lewis acid followed by a methylation step.

DESCRIPTION OF THE INVENTION

The present invention relates to a process for preparing asymmetrical 4,6-bis(aryloxy)pyrimidines derivatives.

Most prior art documents describe that water is non-advantageous and must be removed in order to produce 4,6-bis(aryloxy)pyrimidines derivatives in high yields. Isolation and purification of the end product for example azoxystrobin has been found challenging in various organic solvents. Surprisingly however, it has now been found that a water based reaction substantially free of organic solvents, i.e. less than 10 w/w % compared to the reaction medium content, can be carried out providing excellent yields by the addition of one or more tertiary-amine catalysts to the reaction medium. This provides a clean reaction and produces the desired product in high yields. Water has in addition been found to provide a more easy and convenient workup of the end-product (I), e.g. azoxystrobin.

Using water as a reaction medium is more convenient because of low cost and is much more environmentally friendly in contrast to using an organic solvent.

Accordingly the present invention provides a process for preparing a compound of general formula (I)

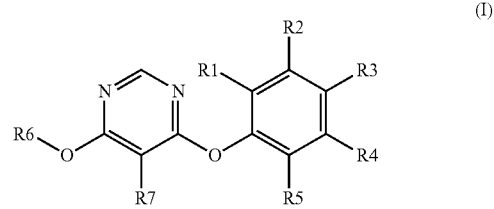

which comprise either:
a) reacting a compound of general formula (II)

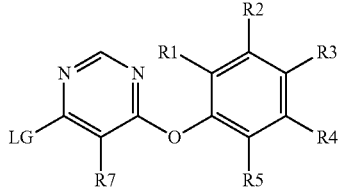
(II)

with an alcohol of the general formula R6-OH, or a salt thereof,
  i) in the presence of between 0.05 and 40 mol % of one or more tertiary-amine catalyst(s); and
  ii) using water as reaction medium and wherein the reaction medium contains less than 10 w/w % of organic solvent;
or
b) reacting a compound of general formula (III)

(III)

with a compound of general formula (IV)

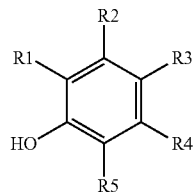
(IV)

or a salt thereof,
  i) in the presence of between 0.05 and 40 mol % of one or more tertiary-amine catalyst(s); and
  ii) using water as reaction medium and wherein the reaction medium contains less than 10 w/w % of organic solvent;
wherein:
LG represents any suitable leaving group known within the art. It is within the skills of an ordinary practitioner to select a suitable leaving group. Typical leaving groups LG includes halogen, preferably chlorine or bromine; C1-C6 alkoxy, preferably methoxy or ethoxy; C1-C6-alkylsulfonyloxy such as methylsulfonyloxy; C1-C6-haloalkylsulfonyloxy such as trifluoromethylsulfonyloxy; arylsulfonyloxy such as phenyl- or naphtylsulfonyloxy, where the aryl radical may, if appropriate, be substituted by one or more halogen or $C_{1-6}$-alkyl groups, such as phenylsulfonyloxy, p-toluenesulfonyl-oxy and p-Cl-phenylsulfonyloxy. LG is preferably chlorine, bromine, C1-C6-alkyl- or phenyl-sulfonyloxy with chlorine being most preferred.
R1, R2, R3 and R4 represent, independently of one another, hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulphonyl;

R5 is hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulponyl, or one of the following radicals:

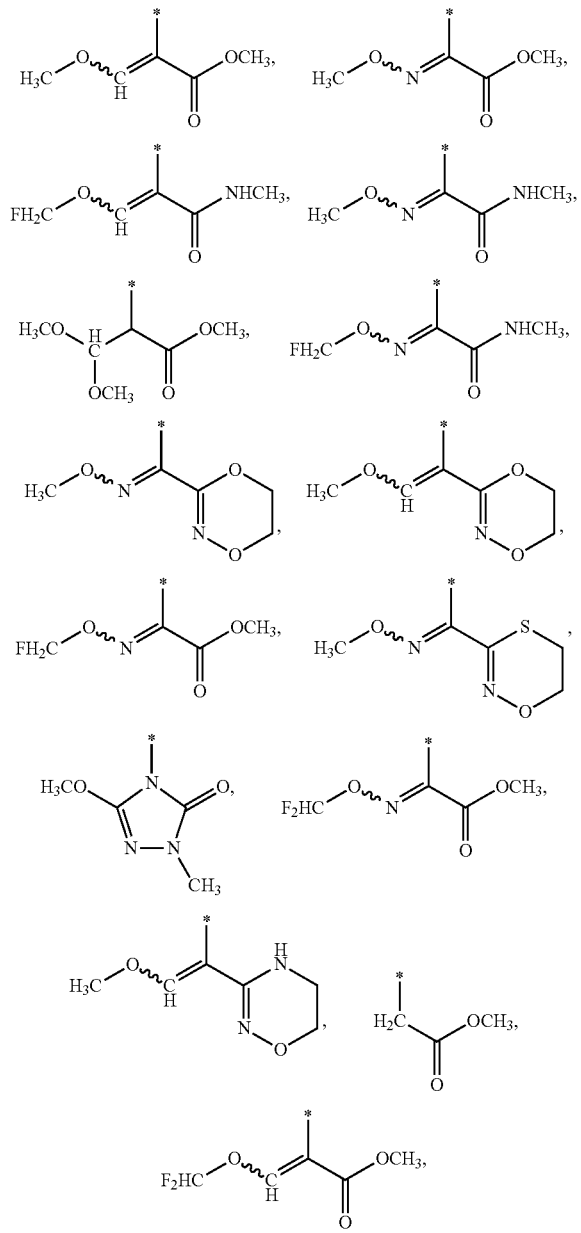

wherein * denotes the point of attachment to the phenyl radical of formula (I);

R6 is substituted or unsubstituted aryl, or substituted or unsubstituted heterocyclyl, or a salt thereof;

R7 is hydrogen, fluorine, chlorine or bromine;

with the proviso that R6 and the radical:

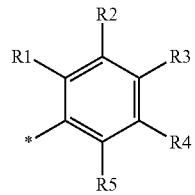

are different from each other.

The catalyst used according to the invention is one or more tertiary amine(s). By a tertiary amine is meant a compound comprising a nitrogen atom having three substitutions different from hydrogen i.e. amines of the formula R'R''R'''N where R', R'' and R''' are each independently C1-C10 (especially C1-C8) alkyl, C3-C6 cycloalkyl, aryl (especially phenyl) or aryl(C1-C4)alkyl (especially benzyl); or two or three of R', R'' and R''' join together with the nitrogen atom to which they are attached to form one, two or three 5-, 6- or 7-membered alicyclic rings optionally fused and optionally containing a second or third ring nitrogen atom. These substituents may comprise one or more substituents independently of one another. In a preferred embodiment of the invention, the tertiary amine is a cyclic amine i.e. an amine of the formula R'R''R'''N where two or three of R', R'' and R''' join together with the nitrogen atom to which they are attached to form one, two or three 5-, 6- or 7-membered alicyclic rings optionally fused and optionally containing a second or third ring nitrogen atom. Again, these cyclic amines may comprise one or more substituents, e.g. as herein defined.

In a preferred embodiment of the invention, there is provided a process wherein the catalyst is chosen among one or more of the following compounds according to general formulae VI to XIV:

a piperidine-based molecule of the general formula (VI)

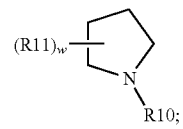

(VI)

or a 1,4-diazabicyclo[2.1.1]hexane-based molecule of the general formula (VII)

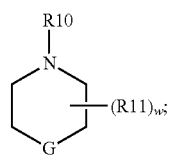

(VII)

or a pyrrolidine-based molecule of the general formula (VIII)

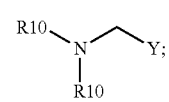

(VIII)

or a tertiary amine-based molecule of the general formula (IX)

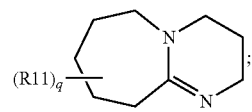

(IX)

or a azepine-based molecule of the general formula (X)

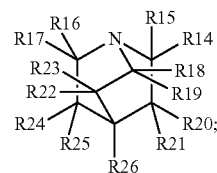

(X)

or a Quinuclidine-based molecules of the general formula (XI)

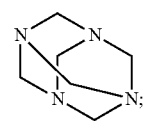

(XI)

or a hexamethylenetetramine of the formula (XII)

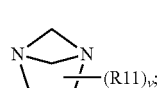

(XII)

or a triazole-based molecule of the general formula (XIII)

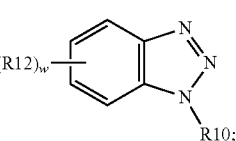

(XIII)

or a 1,4-diazabicyclo[2.2.2]octane-based molecule of the general formula (XIV)

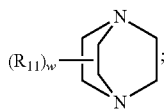

wherein:
q is 0, 1, 2, 3, 4 or 5;
v is 0, 1, 2 or 3;
w is 0, 1, 2, 3 or 4;
X is halogen;
Y is $CH_2N(CH_3)_2$, H, or C1-C4 alkyl;
G is C, S, O or N;
R10 represents, independently, straight or branched alkyl, substituted or unsubstituted benzyl, substituted or unsubstituted phenyl, halogen, cyano, hydroxyl, nitro, alkylcarbonyl, allyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulphonyl;
R11 represents, independently, a substituted or unsubstituted carbon bridge of 1-3 carbon atoms, or represents independently straight or branched alkyl, substituted or unsubstituted benzyl, alkoxy, alcohol, alkenyl, carbonyl, or carboxylate;
R12 represents, independently, $N(CH_3)_2$, C3-C6 substituted or unsubstituted heterocyclyl, substituted or unsubstituted benzyl, substituted or unsubstituted phenyl, straight or branched alkyl, halogen, cyano, nitro, alkylcarbonyl, formyl, alkoxycarbonyl, aminocarbonyl, alkylaminocarbonyl, dialkylaminocarbonyl, or represents optionally halogen-substituted alkyl, aryl, alkoxy, alkylthio, alkylsulphinyl or alkylsulphonyl;
R13 represents a straight or branched C1-C18 alkyl;
R14, R15, R16, R17, R18 and R19 represents, independently of one another, hydrogen, halogen, methyl, methoxy, methylene or cyano; or, independently, R14 and R15, R16 and R17, R18 and R19 together form =O, =S, —N or =C(R30)(R31), wherein R30 and R31 are, independently, hydrogen or R10;
R20, R21, R22, R23, R24 and R25 represents, independently of one another, hydrogen, halogen, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy, optionally substituted silyloxy, or, independently, R20 and R21, R22 and R23 and R24 and R25 together form =O, =S, =N or =C(R30)(R31), wherein R30 and R31 are, independently, hydrogen or R10;
R26 represents hydrogen, halogen, alkenyl, alkynyl, alkylcarbonyl, formyl, alkoxycarbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy or optionally substituted silyloxy;

In another preferred embodiment of the invention, there is provided a process wherein the catalyst is chosen among one or more of the following compounds according to general formulae VI to XIV:

compounds of the general formula (VI) wherein w is 0, 1 or 2; G is either C or O; R10 is alkyl, preferably C1-C4, most preferably methyl; R11 is a substituted or unsubstituted carbon bridge of 1-3 carbon atoms, or is independently straight or branched C1-C4-alkyl, preferably 1 bridging carbon atom; or compounds of the general formula (VII) wherein w is 0 or 1; R11 is a straight or branched alkyl, preferably C1-C4 straight or branched alkyl, and most preferably methyl; or compounds of the general formula (VIII) wherein w is 0 or 1; R10 is straight or branched C1-C6 alkyl, allyl, or substituted or unsubstituted benzyl, preferably straight C1-C3 alkyl, allyl, unsubstituted benzyl, most preferably methyl, allyl or unsubstituted benzyl; R11 is a straight or branched alkyl, carbonyl, or alkenyl, preferably C1-C4 straight or branched alkyl, and most preferably methyl; or compounds of the general formula (IX) wherein R10 is C1-C8 straight or branched alkyl, preferably C1-C4 straight or branched alkyl, and most preferably methyl or ethyl; Y is $CH_2N(CH_3)_2$, H, or C1-C4 alkyl, preferably $CH_2N(CH_3)_2$, H or methyl and most preferably $CH_2N(CH_3)_2$, or H; or compounds of the general formula (X) wherein q is 0 or 1; R11 is C1-C4 alkyl, preferably methyl or ethyl, and most preferably methyl; or compounds of the general formula (XI) wherein the compound is quinuclidine, 3-quinuclidinol or 3-quinuclidinone, or an acid salt thereof; or the compound of formula (XII) is hexamethylenetetramine; or compounds of the general formula (XIII) wherein w is 0 or 1; R10 is hydroxyl, alkoxy or C1-C4 alkyl, preferably hydroxyl, methoxy, or methyl and most preferably hydroxyl; R12 is halogen, cyano, nitro, alkoxy, C1-C4 alkyl, preferably halogen, cyano, nitro, or methyl; or compounds of the general formula (XIV) wherein w is 0, 1, or 2; R11 is a straight or branched alkyl, preferably C1-C4 straight or branched alkyl, and more preferably methyl;

In a more preferred embodiment of the invention, the catalyst is chosen among one or more of the following compounds:

A compound of the general formula (VI) that is N-methylpiperidine or N-methylmorpholine.

A compound of the general formula (VII) that is 1,4-diazabicyclo[2.1.1]hexane.

A compound of the general formula (VIII) that is (1-methylpyrrolidin-2-yl)methanol, 1-allylpyrrolidine, methyl methylprolinate, N-methylpyrrolidine, or methyl benzylprolinate.

A compound based of the general formula (IX) that is N,N,N',N'-tetramethylmethane-diamine or triethylamine.

A compound of the general formula (X) that is 2,3,4,6,7,8,9,10-octahydropyrimido-[1.2-a]azepine.

A compound of the general formula (XII) that is hexamethylenetetramine.

A compound of the general the formula (XIII) that is 1H-benzo[d][1.2.3]triazol-1-ol.

A compound of the general formula (XIV) that is 1,4-diazabicyclo[2.2.2]octane (also referred to as DABCO).

In a most preferred embodiment of the invention, there is provided a process wherein the catalyst is chosen among one or more of the following compounds: 1,4-diazabicyclo[2.2.2]octane (DABCO), N-methylpyrrolidine, N-methylpiperidine, N-methylmorpholine, hexamethylenetetramine, 1,4-diazabicyclo[2.1.1]hexane, quinuclidine, 3-quinuclidinol or 3-quinuclidinone.

In a more preferred embodiment of the invention, there is provided a process for preparing a compound of general formula (I)

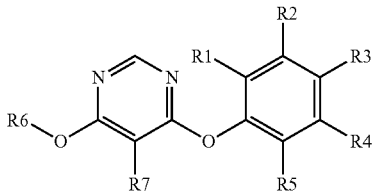 (I)

which comprise reacting a compound of general formula (II)

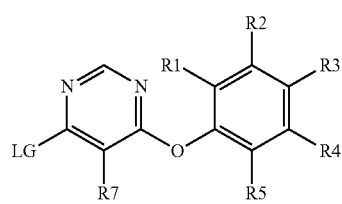 (II)

with an alcohol of the general formula R6-OH, or a salt thereof, i) in the presence of between 0.05 and 40 mol % of one or more tertiary-amine catalyst(s); and ii) using water as reaction medium which is substantially free of organic solvents;

In a preferred embodiment of the invention there is provided a process wherein:

LG represents any suitable leaving group known within the art. It is within the skills of an ordinary practitioner to select a suitable leaving group. Typical leaving groups LG includes halogen, preferably chlorine or bromine; C1-C6 alkoxy, preferably methoxy or ethoxy; C1-C6-alkylsulfonyloxy such as methylsulfonyloxy; C1-C6-haloalkylsulfonyloxy such as trifluoromethylsulfonyloxy; arylsulfonyloxy such as phenyl- or naphtylsulfonyloxy, where the aryl radical may, if appropriate, be substituted by one or more halogen or $C_{1-6}$-alkyl groups, such as phenylsulfonyloxy, p-toluenesulfonyl-oxy and p-Cl-phenylsulfonyloxy. LG is preferably chlorine, bromine, C1-C6-alkyl- or phenyl-sulfonyloxy with chlorine being most preferred.

R1, R2, R3 and R4 are, independently, hydrogen, fluorine, chlorine, bromine, cyano, nitro, acetyl, propionyl, methoxycarbonyl, ethoxycarbonyl, aminocarbonyl, methylaminocarbonyl, ethylaminocarbonyl, dimethylaminocarbonyl, diethylaminocarbonyl, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio, trifluoromethylsulphinyl or trifluoromethylsulphonyl. More preferred there is provided a process wherein R1, R2, R3 and R4 are, independently, hydrogen or methyl. Most preferably R1, R2, R3 and R4 are each hydrogen.

In a preferred embodiment of the invention there is provided a process wherein R5 represents one of the following radicals:

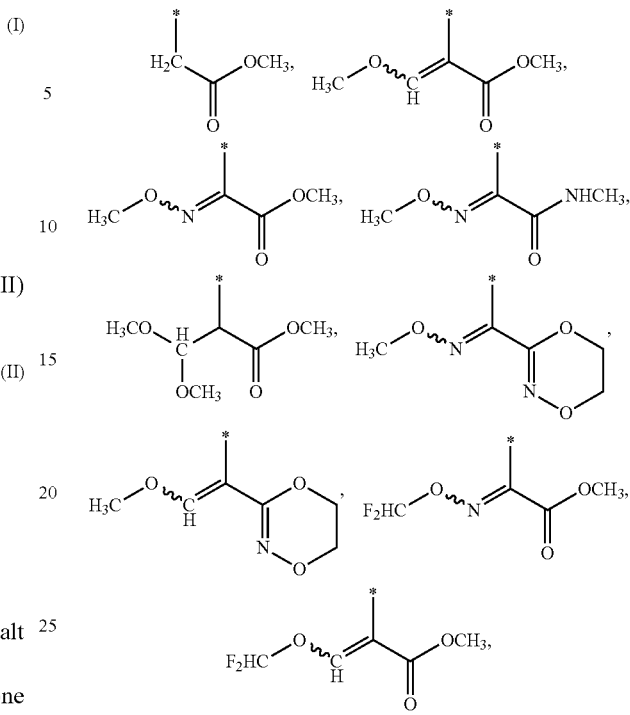

or a mixture thereof, where * denotes the point of attachment to the phenyl radical.

More preferred R5 represents one of the following radicals:

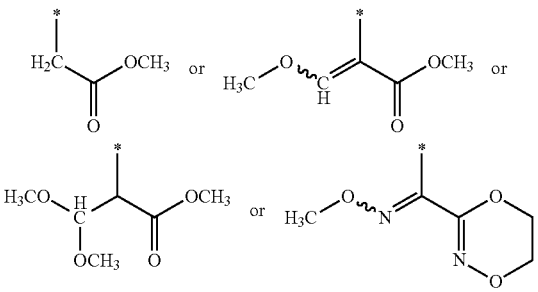

or a mixture thereof, where * denotes the point of attachment to the phenyl radical.

In a preferred embodiment of the invention there is provided a process wherein R6 represents one of the following:

a heterocycle having 3 to 7 ring members, optionally substituted by halogen or by C1-6 alkyl, C1-6 alkoxy, C1-6 halogenoalkyl or C1-6 halogenoalkoxy; or phenyl or naphthyl, each of which is optionally mono- to pentasubstituted by identical or different substituents selected from the group comprising:

a. halogen, cyano, formyl or acetal protected formyl (for example the dimethyl or diethyl acetal, 1,3-dioxolan-2-yl, 1,3-dioxan-2-yl) carboxyl, carbamoyl, thiocarbamoyl, aminocarbonyl;

b. C1-8, straight-chain or branched, alkyl, oxyalkyl, alkoxy, alkoxyalkyl, alkyl-thioalkyl, dialkoxyalkyl, alkylthio, alkylsuphinyl or alkylsulphonyl having in each case 1 to 8 carbon atoms;

c. C2-6, straight-chain or branched, alkenyl or alkenyloxy;
d. C1-6, straight-chain or branched, halogenoalkyl, halogenoalkoxy, halogeno-alkylthio, halogenoalkylsulphinyl or halogenoalkylsulphonyl with between 1 and 13 identical or different halogen atoms;
e. C2-6, straight chain or branched, halogenoalkenyl or halogenoalkenyloxy with between 1 and 11 identical or different halogen atoms;
f. C1-6, straight-chain or branched, dialkylamino, alkylcarbonyl, alkylcarbonyl-oxy, alkoxycarbonyl, alkylaminocarbonyl, dialkylaminocarbonyl, arylalkyl-aminocarbonyl, dialkylaminocarbonyloxy, alkenylcarbonyl or alkynyl-carbonyl;
g. C3-6 cycloalkyl or cycloalkyloxy;
h. doubly attached C3-4 alkylene, C2-3 oxyalkylene or C1-2 dioxyalkylene, each of which is optionally mono- to tetrasubstituted by identical or different substituents selected from the group consisting of fluorine, chlorine, oxo, methyl, trifluoromethyl and ethyl; or
i. the radical

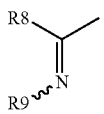

in which:
R8 is hydrogen, hydroxyl, C1-4 alkyl or C1-6 cycloalkyl; and
R9 represents hydroxyl, methoxy, ethoxy, amino, methylamino, phenyl or benzyl; or represents C1-4 alkyl or alkoxy, optionally substituted with cyano-, alkoxy-, alkylthio-, alkylamino-, dialkylamino- or phenyl; or represents C2-4 alkenyloxy or alkynyloxy; or represents benzoyl, benzoylethenyl, cinnamoyl, heterocyclyl; or represents phenylalkyl, phenylalkyloxy or heterocyclylalkyl, having in each case 1 to 3 carbon atoms in the alkyl moieties and being in each case optionally mono- to trisubstituted in the ring moiety by halogen and/or straight-chain or branched C1-4 alkyl or alkoxy.

More preferably R6 is optionally mono- to pentasubstituted phenyl where the substituents are selected from halogen, cyano, formyl or acetal protected formyl, methoxycarbonyl, ethoxy-carbonyl, aminocarbonyl, methylaminocarbonyl, ethylaminocarbonyl, dimethylamino-carbonyl, diethylaminocarbonyl, in each case straight-chain or branched C1-4 alkyl or halogenoalkyl or represents the radical:

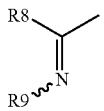

wherein R8 is hydrogen and R9 is hydroxyl, methoxy or ethoxy.

Most preferably R6 is 2-cyanophenyl (i.e. the alcohol of general formula R6-OH is 2-cyanophenol).

In a preferred embodiment of the invention there is provided a process wherein R7 is hydrogen, fluorine or chlorine, most preferably hydrogen. In a preferred embodiment, R1, R2, R3 and R4 are hydrogen, R5 is

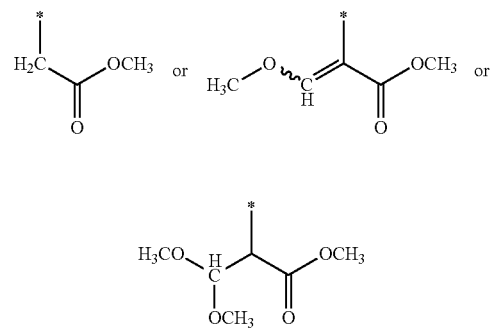

or, or a mixture thereof, R6 is 2-cyanophenyl and R7 is hydrogen.

In the definitions above, and unless specified otherwise:
(a) Saturated or unsaturated hydrocarbon chains, such as alkyl, alkanediyl, alkenyl or alkynyl, may be straight-chain or branched. Suitably, and unless specified otherwise, alkyl and alkyl-derived chains have 1 to 10 carbon atoms and alkenyl and alkenyl-derived chains as well as alkynyl and alkynyl-derived chains have 2 to 10 carbon atoms. Hydrocarbon chains may include heteroatoms (for example, they may be alkoxy, alkylthio or alkylamino groups) and may also be mono- or polysubstituted by e.g. halogen atoms and/or hydroxyl groups (for example halogenoalkyl, halogeno-alkoxy, hydroxyalkyl).
(b) Halogen or halogeno means fluorine, chlorine, bromine or iodine. Suitably, halogen or halogeno means fluorine, chlorine or bromine. Most suitably, halogen or halogeno means fluorine or chlorine.
(c) Aryl groups are aromatic, mono or polycyclic hydrocarbon rings, such as, for example, phenyl, naphthyl, anthranyl, phenanthryl. Suitably aryl groups are phenyl or naphthyl and most suitably are phenyl.
(d) Heterocyclyl groups are saturated or unsaturated (and may be aromatic), cyclic compounds where at least one ring member is a heteroatom, i.e. an atom different from carbon. If the ring contains a plurality of heteroatoms, they may be identical or different. Suitable heteroatoms are oxygen, nitrogen or sulphur. The cyclic components may form a polycyclic ring system together with other carbocyclic or heterocyclic, fused-on or bridged rings. Suitably, heterocyclyl groups may be mono- or bicyclic ring systems, and more suitably, mono- or bicyclic aromatic ring systems. Heterocyclyl groups may also be mono- or polysubstituted, suitably by methyl, ethyl or halogen.
(e) Cycloalkyl groups are saturated carbocyclic compounds, which may form polycyclic ring systems together with other carbocyclic fused-on or bridged rings. Polycyclic ring systems may also be attached to heterocyclic groups or ring systems.

The above mentioned general or preferred radical definitions apply both to the end product of formula (I) and to the starting materials required for the preparation of formula (I).

In a further preferred embodiment, the process of invention comprises reacting a compound of general formula (IIa):

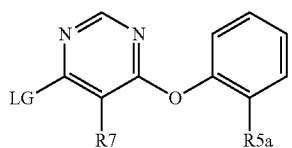

wherein LG and R7 is as previously defined, and R5a is one of the radicals:

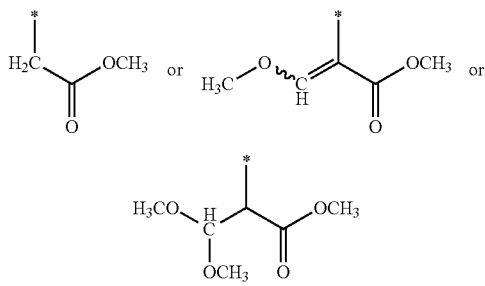

with 2-cyanophenol, or a salt thereof (suitably sodium or potassium 2-cyanophenoxide) in the presence of between 0.05 and 40 mol % of one or more tertiary-amine catalyst as defined above.

In particular, the present invention provides a process for preparing strobilurin fungicides such as methyl (E)-2-{2-[6-(2-cyanophenoxy)-pyrimidin-4-yloxy]phenyl}-3-methoxyacrylate (azoxystrobin), according to formula (Ia)

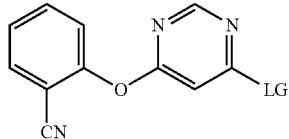

or the intermediates thereof, such as methyl 2-{2-[6-(2-cyanophenoxy)pyrimidin-4-yloxy]phenyl}acetate (DMA) according to formula (Ib).

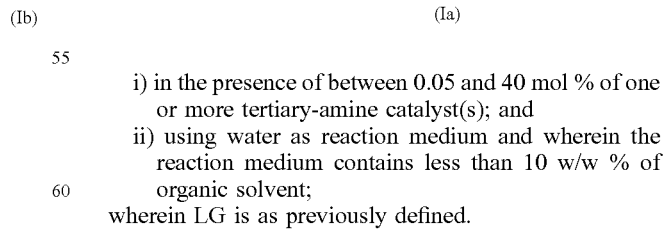

In a very preferred embodiment of the present invention there is provided a process for the preparation of the compound of formula (Ia) which comprise either:

a) reacting 2-cyanophenol with a compound of the formula (II)

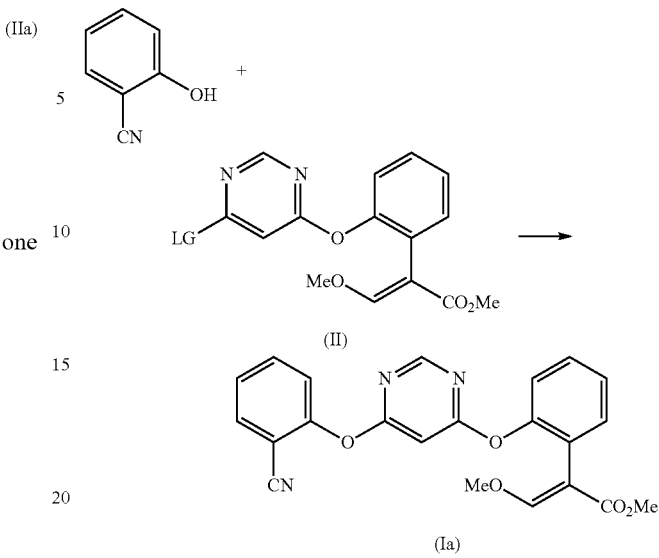

i) in the presence of between 0.05 and 40 mol % of one or more tertiary-amine catalyst(s); and
ii) using water as reaction medium which is substantially free of organic solvents; or b) reacting a compound of formula (III) with a compound of formula (IV) or a salt thereof,

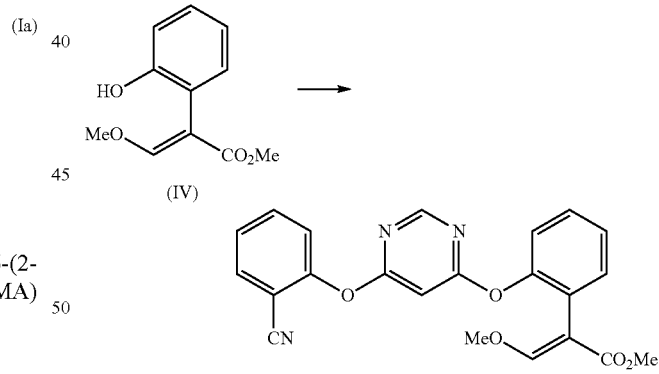

i) in the presence of between 0.05 and 40 mol % of one or more tertiary-amine catalyst(s); and
ii) using water as reaction medium and wherein the reaction medium contains less than 10 w/w % of organic solvent;

wherein LG is as previously defined.

And in yet another very preferred embodiment of the present invention there is provided a process for the preparation of the compound of formula (Ib) which comprise either:

a) reacting 2-cyanophenol with a compound of the formula (II)

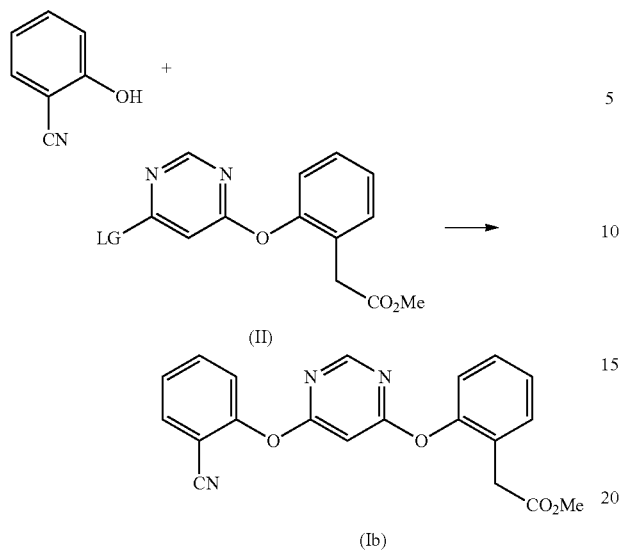

(II)

(Ib)

i) in the presence of between 0.05 and 40 mol % of one or more tertiary-amine catalyst(s); and
ii) using water as reaction medium and wherein the reaction medium contains less than 10 w/w % of organic solvent; or
b) reacting a compound of formula (III) with a compound of formula (IV) or a salt thereof,

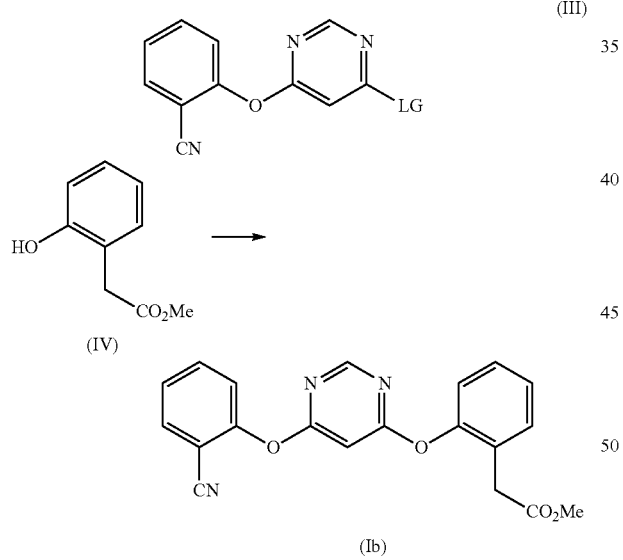

(III)

(IV)

(Ib)

i) in the presence of between 0.05 and 40 mol % of one or more tertiary-amine catalyst(s); and
ii) using water as reaction medium and wherein the reaction medium contains less than 10 w/w % of organic solvent;
wherein LG is as previously defined.

If the product of the invention is a compound of general formula (Id) (i.e. compound (I) wherein R5 is methylpropionate), then this compound (Id) can be converted to the compound of general formula (If) (i.e. compound (I) wherein R5 is methyl 2-(3-methoxy)acrylate);

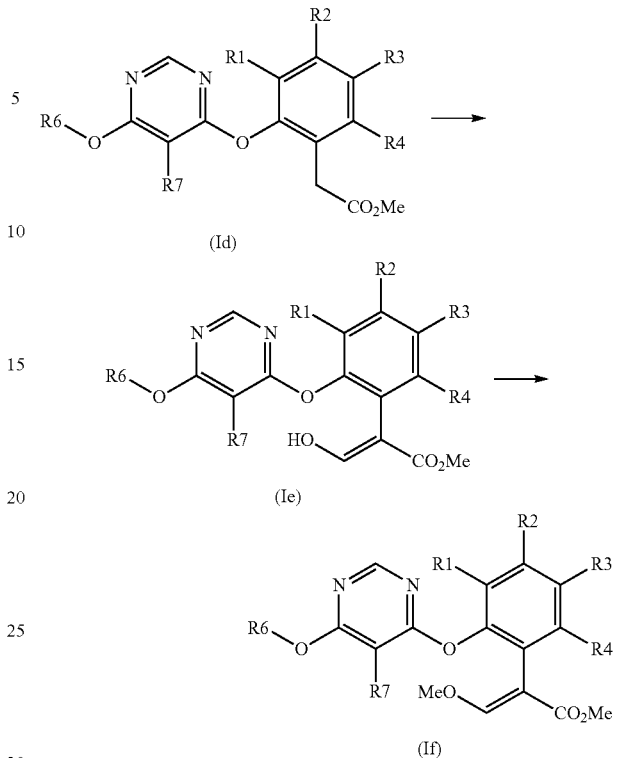

(Id)

(Ie)

(If)

Accordingly, the invention further relates to a process for the preparation of a compound of general formula (If)

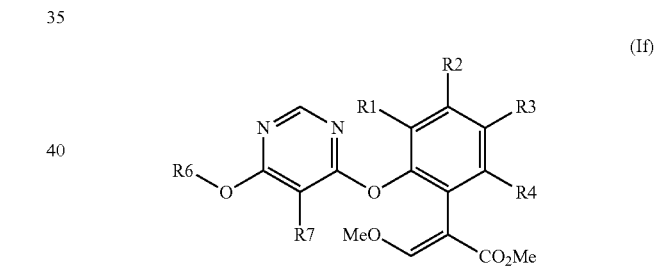

(If)

which comprise either:
a) reacting a compound of general formula (IId)

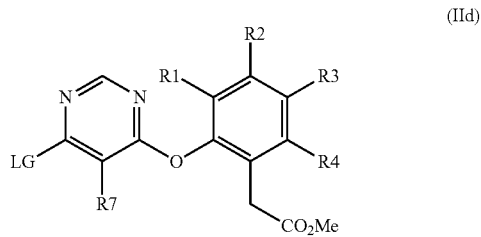

(IId)

with an alcohol of the general formula R6-OH, or a salt thereof,
i) in the presence of between 0.05 and 40 mol % of one or more tertiary-amine catalyst(s); and
ii) using water as reaction medium and wherein the reaction medium contains less than 10 w/w % of organic solvent; or b) reacting a compound of general formula (III)

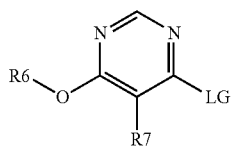

with a compound of general formula (IVd)

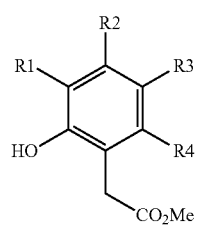

or a salt thereof,
i) in the presence of between 0.05 and 40 mol % of one or more tertiary-amine catalyst(s); and
ii) using water as reaction medium and wherein the reaction medium contains less than 10 w/w % of organic solvent;
as to prepare a compound of general formula (Id)

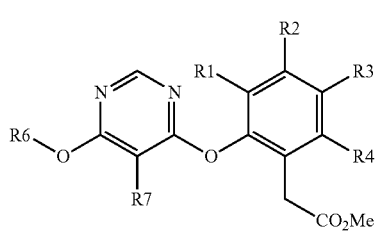

and converting the compound of general formula (Id) through a formylation step to the compound of general formula (Ie) and converting this compound of general formula (Ie) through a methylation step and optionally isolation and purification of compound (If);
wherein:
LG, R1, R2, R3, R4, R6 and R7 are as previously defined.

In the preparation of a compound of general formula (If): The compound of the general formula (Id) is first converted through a formylation step conducted in a solvent (e.g. aprotic organic solvent) in the presence of a formylating agent, a Lewis acid, and a base (preferably an organic base) at a temperature ranging from −20 to 200° C., so that the compound of general formula (Ie) is obtained. Isolation and purification of the compound of general formula (Ie) might not be necessary however this is dependent on the specific reaction conditions used in both the formylation and methylation steps. The methylation step is conducted in the presence of a methylating agent and an alkali at a temperature ranging from −20 to 100° C. to obtain the compound of general formula (If).

Examples of the Lewis acid are titanium tetrachloride, aluminum trichloride, methylaluminum chloride, tin chloride, ferric chloride, zinc chloride and boron trifluoride ethyl ether, preferably titanium tetrachloride. The amount of the Lewis acid used should ensure the smoothness of the formylation step, for example, 0.1 to 6.0 molar equivalent, preferably 1.0 to 3.0 molar equivalent, per 1.00 molar equivalent of the compound of general formula (Id) used.

Examples of the formylating agent are methyl formate, ethyl formate, trimethyl orthoformate and triethyl orthoformate, preferably trimethyl orthoformate. The amount of the formylating agent used should ensure the smoothness of the formylation step, for example, 1.0 to 10.0 molar equivalent, preferably 1.0 to 3.0 molar equivalent, per 1.00 molar equivalent of the compound of general formula (Id) used.

Examples of the organic base are amines and metal alkoxides, preferably tertiary amine like trimethyl amine, triethyl amine, tributyl amine, diisopropylethyl amine, pyridine. The amount of the organic base used should ensure the smoothness of the reaction, for example, 0.2 to 10.0 molar equivalent, preferably 2.0 to 6.0 molar equivalent, per 1.00 molar equivalent of the compound of general formula (Id) used.

Examples of the alkali are sodium hydroxide, potassium hydroxide, sodium carbonate, potassium carbonate, sodium bicarbonate, potassium bicarbonate, sodium methoxide, sodium ethoxide and sodium tertiary butoxide, preferably sodium hydroxide and potassium hydroxide. The amount of the alkali used should ensure the smoothness of the methylation step, for example, 0.8 to 6.0 molar equivalent, preferably 1.0 to 2.0 molar equivalent, per 1.00 molar equivalent of the compound of general formula (Id) used. Examples of the methylating agent are dimethyl sulfate, trimethyl orthoformate, chloromethane, bromomethane and iodomethane, preferably dimethyl sulfate. The amount of the methylating agent used should ensure the smoothness of the methylation step, for example, 0.8 to 6.0 molar equivalent, preferably 1.0 to 3.0 molar equivalent, per 1.00 molar equivalent of the compound of general formula (Id) used.

It is preferable to conduct the formylation step in an aprotic solvent, which is unable to donate or accept protons. The example of aprotic solvent includes halogenated hydrocarbon, benzene, saturated hydrocarbon, dimethyl sulfoxide, preferably halogenated hydrocarbon such as dichloroethane, dichloromethane, trichloromethane and chlorobenzene.

The medium suitable for conducting the methylation step may be a polar or a non-polar solvent, such as benzene, toluene, chlorobenzene, dichloromethane, dichloroethane, methanol, ethanol, butanol, ethyl ether, 1,2-dimethoxyethane, tetrahydrofuran, acetone, methyl ethyl ketone, methyl isobutyl ketone, ethyl acetate, isopropyl acetate, propyl acetate and butyl acetate.

In a preferably embodiment the compound of the general formula (Id) is the compound of formula (Ib) and the compound of the general formula (If) is the compound of formula (Ia), i.e. a process that comprise the following sequence as shown below:

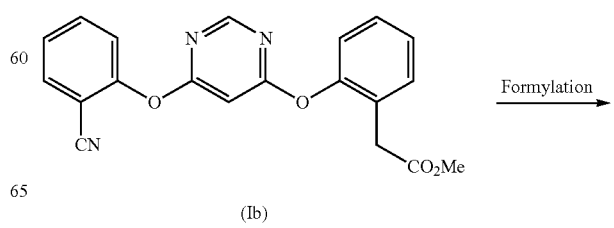

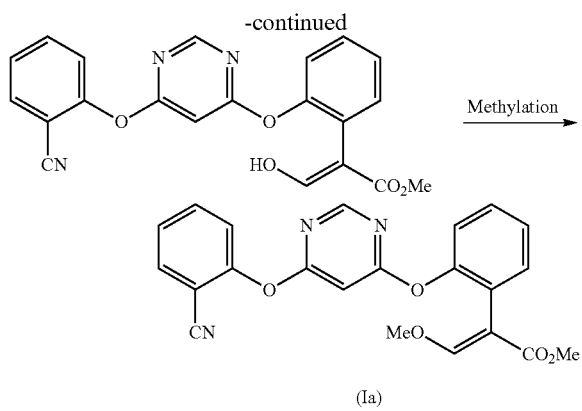

(Ia)

The starting materials R6-OH and the compounds of formulae (II), (III), (IV) and the end product of formula (I) can be present as pure isomers of different possible isomeric forms, for example E or Z isomers or, as appropriate, as mixtures of different possible isomeric forms, in particular of hetero-isomers, such as for example, E/Z mixtures.

The process of the invention is carried out using water as the reaction medium which is substantially free of any organic solvents. By the term "substantially free" is meant that the reaction medium contains less than 10 w/w % of organic solvent compared to the reaction medium content.

In a preferred embodiment, the reaction medium contains less than 9 w/w % of organic solvent, preferably less than about 8 w/w % of organic solvents, more preferably less than 7 w/w % organic solvents, even more preferably less than 6 w/w % organic solvents, and most preferably less than 5 w/w % of organic solvent.

In a more preferred embodiment, the reaction medium contains less than 4.5 w/w % of organic solvent, preferably less than about 4 w/w % of organic solvents, more preferably less than 3 w/w % organic solvents, even more preferably less than 2 w/w % organic solvents, and most preferably less than 1 w/w % of organic solvent.

In an even more preferred embodiment, the reaction medium contains less than 0.9 w/w % of organic solvent, preferably less than about 0.8 w/w % of organic solvents, more preferably less than 0.6 w/w % organic solvents, even more preferably less than 0.5 w/w % organic solvents, and most preferably less than 0.4 w/w % of organic solvent.

In a most preferred embodiment, the reaction medium contains less than 0.3 w/w % of organic solvent, preferably less than about 0.2 w/w % of organic solvents, more preferably less than 0.1 w/w % organic solvents, even more preferably less than 0.05 w/w % organic solvents, and most preferably is completely free of organic solvents.

If any organic solvents are present they may have been present in the starting materials, e.g. from previous process steps required to prepare the starting materials and/or in the production equipment (reactors, pipes etc.) from prior use. Accordingly, the process of the invention is carried out with less than 10 w/w % organic solvent, preferably no organic solvent, being present/added, deliberately or not, in the reaction media and preferably under such conditions that the starting materials and reaction equipment used is as free from traces of organic solvent as is practically possible.

Examples of such organic solvents are aliphatic, alicyclic and aromatic hydrocarbons, such as petroleum ether, hexane, heptane, cyclohexane, methylcyclohexane, benzene, toluene, xylene and decalin; halogenated hydrocarbons, such as chlorobenzene, dichlorobenzene, dichloromethane, chloroform, carbon tetrachloride, dichloroethane and trichloroethane; heteroaromatic solvents such as pyridine or a substituted pyridine, for example 2,6-dimethylpyridine; ethers, such as diethyl ether, diisopropylether, methyl-tert-butyl ether, methyl-tert-amyl ether, dioxane, tetrahydrofuran, 1,2-dimethoxyethane, 1,2-diethoxyethane and anisole; ketones, such as acetone, butanone, methyl isobutyl ketone and cyclohexanone; nitriles, such as acetonitrile, propionitrile, n- and i-butyronitrile and benzonitrile; amides, such as N,N-dimethylformamide, N,N-dimethylacetamide, N-methylformamide, N-methyl-pyrrolidone and hexamethylphosphoric triamide; esters, such as methyl acetate, ethyl acetate and isopropyl acetate; sulphoxides, such as dimethylsulphoxide; sulphones, such as dimethylsulphone and sulpholane; alcohols such as ethanol, methanol, butanol or iso-propanol.

Within the meaning of this invention, any tertiary-amine compound that is capable of catalyzing the reaction is regarded as a catalyst. The tertiary-amine is so selected as to remain inert, other than its catalytic effect, under the reaction conditions i.e. it does not react with any of the starting materials or end-products. As such the catalyst or the reaction medium comprising the catalyst may be reused multiple times.

By organic solvent is meant any solvent, different from water, which is liquid at ambient temperature and inert under the reaction condition herein described. Within the meaning of this invention any of the starting materials, intermediates, products or catalysts are not considered part of the reaction medium.

In addition, the process of the invention is preferably carried out in the presence of an acid acceptor. Suitable acid acceptors are all customary inorganic and organic bases. These include, for example, alkaline earth metal hydroxides and alkali metal hydroxides, acetates, carbonates, bicarbonates phosphates, hydrogen phosphates and hydrides such as sodium hydroxide, potassium hydroxide, sodium acetate, potassium acetate, sodium carbonate, potassium carbonate, sodium bicarbonate, potassium bicarbonate, potassium phosphate, potassium hydrogen phosphate, sodium phosphate, potassium hydrogen phosphate, calcium hydride, sodium hydride and potassium hydride, guanidines, phosphazines (see, for example, Liebigs Ann. 1996, 1055-1081), prophosphatranes (see, for example, JACS 1990, 9421-9422), metal dialkylamides such as lithium di-iso-propylamide and tertiary amines such as those described above as possible solvents or diluents. Particularly suitable acid acceptors are the alkaline earth metal, alkali metal hydroxides and alkali metal carbonates, especially potassium hydroxide, potassium carbonate and sodium carbonate. More suitably, the acid acceptor is potassium carbonate or potassium hydroxide. The amount of acid acceptor used is between 0.2 to 5 equivalence of acid acceptor compared to the alcohol of general formula R6-OH or the compound of the general formula (IV), preferably the amount of acid acceptor used is between 0.5 to 4, and most preferably between 1 to 3.

Suitably, the process of the invention is carried out in the presence of between 0.05 and 40 mol % of catalyst, the catalyst being selected among one or more compound(s) of the general formulae (VI) to (XIV). Preferably, any amount of catalyst between 0.1 and 30 mol % of catalyst, or between 0.1 and 20 mol % of catalyst, or between 0.1 and 10 mol % of catalyst is suitable for use in the present invention but, most suitably, between 0.2 and 7 mol % of catalyst is used.

The mol percentage of catalyst present during the reaction is based on the starting compound present in the lowest amount.

Examples are provided below:

| Catalyst | Catalyst loading | Preferred catalyst loading | Most preferred catalyst loading |
|---|---|---|---|
| DABCO | 0.05-40 mol % | 0.1-20 mol % | 0.1-10 mol % |
| Quinuclidine-hydrochloride | 0.05-40 mol % | 0.1-20 mol % | 0.1-10 mol % |
| 3-Quinuclidinol hydrochloride | 0.05-40 mol % | 0.1-20 mol % | 0.1-10 mol % |
| N-methyl-pyrrolidine | 0.05-40 mol % | 0.1-20 mol % | 0.1-10 mol % |
| N-methyl-piperidine | 0.05-40 mol % | 0.1-20 mol % | 0.1-10 mol % |
| 1,4-iazabicyclo[2.1.1]-hexane | 0.05-40 mol % | 0.1-20 mol % | 0.1-10 mol % |

The reaction may be carried out at various temperatures, e.g. temperatures ranging from 50 to 130° C., suitably at a temperature of from 60 to 125° C., and typically at a temperature from 70 to 120° C., for example, from 80 to 110° C.

The process of the invention can be carried out at any pressure depending on the catalysts, base and reaction temperature, but suitably between 1-10 Bar. For catalysts with a low boiling point, higher temperatures can be accessed by reaction at higher pressure than atmospheric pressure, and reactions can be carried out at atmospheric pressure if desired. In general, the reaction may be carried out at a pressure of from 1 to 8 Bar, suitably at the pressure of from 1 to 5 Bar, typically at a pressure of from 1 to 2 Bar, for example at ambient pressure.

For carrying out the process of the invention, from 0.8 to 5 mol, usually from 0.9 to 3 mol, and preferably 0.95 to 1.2 mol of alcohols of general formula R6-OH is employed per mol of the compound of general formula (II); and similar amounts (0.8 to 5 mol, usually from 0.9 to 3 mol) of a compound of general formula (IV) are employed per mole of the compound of general formula (III).

For carrying out the process of the invention, the amount of water used as reaction medium is preferably present in a ratio (w/w) compared to any one of the starting materials compounds (i.e. the coupling components) present in the highest weight amount, of water:coupling-component of higher than 0.2:1, that is, there is preferably more than 0.2 parts water by weight per 1 part by weight of any one the two couplings components present in the highest weight amount. As such there is no upper limit on the total weight/volume of water present as reaction media, but to ease handling of the process and/or workup of the end-product, there is preferably less than 10 parts by weight of water per 1 part of any one the two couplings components present in the highest weight amount, preferably less than 6 and more preferably less than 4 parts water. A preferred ratio between water and the coupling component present in the highest weight amount (water:coupling-component) is from 10:1 to 1:5, preferably from 6:1 to 1:4 and most preferably from 4:1 to 1:3.

The coupling-components are pairwise present in the reaction medium and are either, depending on reaction sequence, a) R6-OH and the compound of general formula (II) or b) the compound of general formula (III) and the compound of general formula (IV).

The process of the invention is carried out by mixing both coupling components used for the reaction optionally together with the acid acceptor at ambient temperature. Water and the catalyst (all or in part) are then added to the reaction mixture and the reaction mixture is stirred, normally at an elevated temperature. However, the catalyst may be added at any stage (all or in part) to start the reaction. After the reaction is judged to be complete, by e.g visual or analytical means, the reaction mixture is worked up and the product is isolated using conventional techniques well known in the art. As stated above, the catalyst may be added at any stage (all or in part) but it is preferable that the catalyst is not mixed with the compound of general formula (II) or the compound of general formula (III) in the absence of the alcohol of general formula R6-OH or absence of the compound of general formula (IV), respectively. The most preferable order of addition is addition of the alcohol of general formula R6-OH or the compound of general formula (IV) to the reaction mixture containing water and base, followed by addition of either the catalyst and/or a compound of the general formula (II) or the compound of general formula (III). Following this order of addition tends to promote higher product yields.

The alcohols of general formula R6-OH required as starting materials for carrying out the process according to the invention are commercially available or can be made from commercially available starting materials using literature processes.

The compounds of formula (II) and (III) may be prepared, for example, as discussed in U.S. Pat. No. 6,734,304 (the contents of which are herein incorporated by reference). In particular, the compound of formula (II), where R5 is the methyl (E)-2-(3-methoxy)acrylate group $C(CO_2CH_3)$=$CHOCH_3$, and the compound of formula (II) where R5 is the methyl 2-(3,3-dimethoxy)propanoate group $C(CO_2CH_3)CH(OCH_3)_2$, may be prepared as described in the international patent publication no. WO 92/08703 from the reaction of 3-(α-methoxy)methylenebenzofuran-2(3H)-one (derived from benzofuran-2(3H)-one) with 4,6-dichloropyrimidine. The compound of formula (II), where R5 is the methyl (E)-2-(3-methoxy)acrylate group, may also be prepared by eliminating methanol from (that is, by the demethanolysis of) the compound of formula (II) where R5 is the methyl 2-(3,3-dimethoxy)propanoate group, as described in the international patent publication nos. WO 92/08703 or WO 98/07707. The compound of formula (II), where R5 is the methyl 2-(3,3-dimethoxy)propanoate group, maybe prepared as described in British patent publication no. GB-A-2291874 by reacting a compound of formula (IV), where R5 is the methyl 2-(3,3-dimethoxy)propanoate group, with 4,6-dichloropyrimidine. It may be purified before use by known techniques or may be used in an unpurified state from a previous reaction, for example, in a 'one-pot' reaction.

The compounds of general formula (IV) are also known and may be prepared by known methods, references to which are given in U.S. Pat. No. 6,734,304. In particular, the compound of formula (IV), where R5 is the methyl 2-(3,3-dimethoxy)-propanoate group, may be prepared as described in GB-A-2291874 from 3-(α-methoxy)-methylenebenzofuran-2(3H)-one. The compound of formula (IV), where R5 is the group methyl (E)-2-(3-methoxy)acrylate, may be prepared by the procedure described in the European patent no. EP-242081 or by the demethanolysis of the compound of formula (IV) where R5 is the methyl 2-(3,3-dimethoxy) propanoate group. In this case the phenolic group needs to be protected by, for example, benzylation before demethanolysis and then de-protected.

If a salt of the alcohol starting material is desired (R6-OH or the compound (IV)), this can be generated in-situ or prior to the reaction taken place e.g. by reacting the alcohol with an acid acceptor.

The following examples illustrate the invention. The examples are not intended as necessarily representative of the overall testing performed and are not intended to limit the invention in any way.

EXAMPLES

In these examples:
DABCO: 1,4-diazabicylclo[2.2.2]octane
DMF: dimethylformamide
DMSO: dimethyl sulfoxide Example 1

In a 500 mL flask equipped with a magnetic stirrer, (E)-methyl 2-(2-((6-chloropyrimidin-4-yl)oxy)phenyl)-3-methoxyacrylate (100 g, 97% pure, 302 mmol), 2-hydroxybenzonitrile (41 g, 341 mmol) and potassium carbonate (25.08 g, 181 mmol) were added. Water (50 mL) and N-methylpiperidine (2.86 g, 28.8 mmol) were added at ambient temperature, then the mixture was placed on an oil bath at ambient temperature and heating begun. The mixture was heated to 120° C. over 20 min and stirring begins once the external temperature is approx. 80° C. Some gas evolution was noted. The mixture was stirred at 100° C. for 5 h, under a mild reflux. The mixture was then cooled to 80° C. and diluted with ethyl acetate (200 mL) and then with water (100 mL). The two phases were stirred and separated. The upper organic portion was evaporated to dryness under vacuum at 40° C. The crude residue was dissolved in methanol (200 mL) at reflux, then water (30 mL) was added slowly at that temperature. The solution was allowed to cool freely with agitation to ambient temperature over 1 h and the solution was seeded with 0.4 g pure azoxystrobin at 40° C. The resulting slurry was further cooled to 0° C. over 20 min, and held there for a further 20 min, then the solids were recovered by suction filtration and washed with 50 mL cold methanol:water 4:1. The filter cake was dried under vacuum at ambient temperature overnight, affording the product azoxystrobin (114.68 g, 97% pure, 91.2% yield) as a free flowing pale brown powder.

Example 2

In a 250 mL flask equipped with a magnetic stirrer, 2-hydroxybenzonitrile (20.5 g, 170 mmol) was suspended in water (20.5 g), then a solution of potassium hydroxide (11.25 g, 85%, 170 mmol) in water (9.5 mL) was added over 2 min, and the mixture became homogeneous. (E)-Methyl 2-(2-((6-chloropyrimidin-4-yl)oxy)phenyl)-3-methoxyacrylate (50 g, 151 mmol) and N-methylpiperidine (2.0 ml, 16.46 mmol) were added, then the resulting slurry was heated to 100° C. under a reflux condenser for 4½ h. The mixture was allowed to cool to 89° C. over 30 min, and then toluene (100 mL) and water (50 mL) were added. The two phases were stirred for 10 min, then stirring was halted and phase separation was rapid. The lower aqueous phase was removed, and then the upper organic portion was evaporated to dryness by rotary evaporation at 60° C. The residue was dissolved in methanol (100 g) at 55° C., and then water (20 g) was added, followed by 0.2 g pure solid azoxystrobin. The mixture was allowed to cool freely to room temperature (RT) with agitatation and left this way overnight. The resulting slurry was further cooled to 0° C. and agitated for 30 min. The solids were recovered by suction filtration, washed with 15 mL cold methanol:water 5:1 and then dried under vacuum at ambient temperature overnight, affording the product azoxystrobin (54.21 g, 97.4% purity, 131 mmol, 86.6% yield).

Example 3

In a 500 mL flask equipped with a magnetic stirrer was placed 2-hydroxybenzonitrile (41 g, 341 mmol), potassium carbonate (25.08 g, 181 mmol) and water (100 mL). The mixture was heated to 70° C. and stirred at that temperature for 10 min. (E)-methyl 2-(2-((6-chloropyrimidin-4-yl)oxy) phenyl)-3-methoxyacrylate (100 g, 302 mmol) was added (caution, rapid $CO_2$ evolution can occur) and 1-methylpyrrolidine (0.629 ml, 6.05 mmol) was added last. The mixture was heated on an oil bath at 120° C. (internal temp 115-117° C.) whereby a light reflux was observed. The mixture was held at 120° C. for 5 h, then cooled to 80° C. and diluted with toluene (200 mL) and water (50 mL). The two phases were separated at that temperature and the upper organic phase was evaporated to dryness in vacuo at 60° C. When the bulk of the toluene had been removed the syrup residue was dissolved in methanol (100 mL) then allowed to cool to ambient temperature under agitation. The resulting slurry was further cooled to 0° C. over 15 min, then filtered. The solids were washed with cold methanol (20 mL) and dried under vacuum affording 110.35 g of azoxystrobin (97.4% pure, 266 mmol 88.1% yield), as a beige solid.

Example 4

In a 50 mL flask, 2-hydroxybenzonitrile (4.1 g, 34.1 mmol) was suspended in water (4.1 g), and then the suspension heated on an oil bath to 70° C. A 50% solution of potassium hydroxide (3.82 g, 34.1 mmol) was added over 2 min, and the mixture became homogeneous. (E)-methyl 2-(2-((6-chloropyrimidin-4-yl)oxy)phenyl)-3-methoxyacrylate (10 g, 97%, 30.2 mmol) and DABCO (0.068 g, 0.605 mmol) were added, then the resulting slurry was heated to 120° C. under a reflux condenser for 3 h. The mixture was allowed to cool to 80° C. over 30 min, then ethyl acetate (20 mL) and water (15 mL) were added, and the two phase mixture was stirred and an emulsion formed. This was allowed to cool to ambient temperature, then 0.5 g potassium carbonate was added and phase separation was rapid. The organic portion was evaporated to dryness in vacuo to give an amber oil (12.86 g, 91.5% purity of azoxystrobin, 29.2 mmol, 96.5% crude yield) that solidified upon standing.

Example 5

In a 250 mL flask, 2-hydroxybenzonitrile (20.5 g, 170 mmol) was suspended in water (15 g), at ambient temperature. A 85% solution of potassium hydroxide (11.25 g, 170 mmol) in water (9.5 mL) was added over 2 min, and the mixture became homogeneous. N-Methylpiperidine (1.5 ml, 12.34 mmol) was added, followed by (E)-methyl 2-(2-((6-chloropyrimidin-4-yl)oxy)phenyl)-3-methoxyacrylate (50 g, 97%, 151 mmol) while ensuring stirring was maintained, then the resulting slurry was heated on an oil bath set to 120° C. under a reflux condenser for 4½ h. The mixture was allowed to cool to 89° C. over 30 min, and then n-butylacetate (100 mL) and water (50 mL) were added. The two phases were stirred for 10 min, then stirring was halted and phase separation was rapid. The lower aqueous phase was removed, then upper organic phase was transferred to a rotary evaporator and 10 mL was removed by distillation at approx 60° C. to remove trace water content. A further 50 mL n-butyl acetate was added, then material was seeded with pure azoxystrobin (200 mg) then allowed to cool to ambient temperature under agitation, then further cooled to 0° C. for 10 min. The solids were recovered by suction filtration and washed with cold n-butyl acetate (20 mL) then dried under vacuum at ambient temperature for two days, affording the product azoxystrobin (63.20 g, 84.9% purity, 133 mmol, 88% yield).

Example 6

2-hydroxybenzonitrile (98% purity, 5.2 g, 42.8 mmol) was suspended as a slurry in water (5.2 mL) and then a solution of potassium hydroxide (85% purity, 2.70 g, 40.9 mmol) in water (2.7 g) was added dropwise at ambient temperature. Methyl 2-(2-((6-chloropyrimidin-4-yl)oxy)phenyl)acetate (74.5% purity, 10.0 g, 26.7 mmol) and finally DABCO (0.08 g, 0.713 mmol) were added, then the mixture was heated to 100° C. for 90 min, then cooled to 60° C. EtOAc (25 mL) was added, followed by 5% aqueous $K_2CO_3$ (20 mL), then the two phases were stirred well and allowed to cool to RT. After 15 min, the two phases were separated, and the organic portion was evaporated to dryness in vacuo affording a semi-sold brown residue. The residue was suspended in methanol (17 g) and heated to 60° C. whereby all material dissolved. The solution was allowed to cool freely to RT under agitation, and the resulting slurry was further cooled to 0° C. The solids were recovered by filtration and washed with cold methanol (5 mL) and then dried under vacuum at ambient temperature affording 10.10 g of DMA, (91.1% purity, 25.5 mmol, 95% yield).

Example 7

2-hydroxybenzonitrile (98% purity, 5.2 g, 42.8 mmol) was suspended as a slurry in water (5.2 mL) and then a solution of potassium hydroxide (85% purity, 2.70 g, 40.9 mmol) in water (2.7 g) was added dropwise at ambient temperature. Methyl 2-(2-((6-chloropyrimidin-4-yl)oxy)phenyl)acetate (74.5% purity, 10.0 g, 26.7 mmol) and finally 1-Methylpiperidine (1.5 ml, 12.34 mmol) were added, then the mixture was heated to 100° C. for 4 hours, then cooled to 60° C. EtOAc (25 mL) was added, followed by 5% aqueous $K_2CO_3$ (20 mL), then the two phases were stirred well and allowed to cool to RT. After 15 min, the two phases were separated, and the organic portion was evaporated to dryness in vacuo affording a semi-sold brown residue. The residue was suspended in methanol (17 g) and heated to 60° C. whereby all material dissolved. The solution was allowed to cool freely to RT under agitation, and the resulting slurry was further cooled to 0° C. The solids were recovered by filtration and washed with cold methanol (5 mL) and then dried under vacuum at ambient temperature affording 9.58 g of DMA, (23.8 mmol, 89% yield).

Example 8

To a jacketed 500 mL reaction vessel with temperature control, condenser and mechanical stirrer was added 173 g $CH_2Cl_2$ and cooled to 0° C. Then 49.9 g $TiCl_4$ (1.315 eq) was added and to the resulting clear solution was added at 0° C. 18.2 g (1.5 eq) methylformate using a dropping funnel. After 15 min at 0-5° C. a solution of methyl 2-{2-[6-(2-cyanophenoxy)pyrimidin-4-yloxy]phenyl}acetate (DMA) (76.0 g 95% pure) in 130 g $CH_2Cl_2$ was added with a dropping funnel over 30 minutes at 0-5° C. resulting in a dark brown mixture. Upon stirring of this mixture at 0-5° C. for 30 minutes 50.6 g (2.5 eq) triethylamin was added over 2 hours at 0-5° C. using a syringe pump. The solution is turning dark and is stirred for 60 minutes at 0-5° C. Reaction mixture is quenched carefully by addition of 400 mL water at 5-15° C. The temperature is allowed to rise to 20-25° C. over 30 minutes under stirring and the phases are separated. To the organic layer is added 497 g of a 10.6% $Na_2CO_3$-solution, 34.6 g (1.5 eq) dimethylsulfate and 6.21 g (0.1 eq) tetrabutylammonium hydrogensulfate at 25° C. This mixture is stirred viguorously for 1 hour at 25-30° C. and the phases are separated. The organic phase is mixed with 228.3 g 40% aqueous $Na_2S_2O_3*5H_2O$ (2.0 eq) and stirred for 2½ hours at 25° C. to remove excess of dimethylsulfate. The phases are separated and the organic phase is washed with 200 mL 1N HCl, concentrated in vacuo and the residue recrystallised from 110 g MeOH. The resulting pale yellow crystals are dried to yield 66.5 g Azoxystrobin of 97% purity.

Comparative Example 1

In a 250 mL flask equipped with a magnetic stirrer was placed (E)-methyl 2-(2-((6-chloropyrimidin-4-yl)oxy)phenyl)-3-methoxyacrylate (50 g, 151 mmol), 2-hydroxybenzonitrile (20.5 g, 170 mmol) and potassium carbonate (12.54 g, 91.0 mmol). Water (25 ml) was added at ambient temperature, then the mixture was placed on an oil bath, the temperature raised to 120° C. and stirred at that temperature for 22 h. The oil bath temperature was lowered to 90° C., then toluene (100 mL) and water (50 mL) were added slowly, while ensuring that good stirring was maintained. The lower aqueous phase was removed and discarded. The upper organic phase was evaporated to dryness on a rotary evaporator at 60° C. The material was dissolved in methanol (85 mL) at 50° C., then allowed to cool under agitation. The mixture was seeded at 30° C. with 0.1 g azoxystrobin, then cooled to 0° C. and held there for 30 min. The crystals were recovered by filtration and washed with cold methanol (15 mL), and then dried under vacuum affording 45.90 g azoxystrobin (97% pure, 110 mmol, 73% yield) as a pale yellow solid.

Comparative Example 2

In a 500 mL flask equipped with a magnetic stirrer, (E)-methyl 2-(2-((6-chloropyrimidin-4-yl)oxy)phenyl)-3-methoxyacrylate (96.2 g, 97%, 300 mmol) was dissolved in dimethylformamide (106 ml) and then a solution of 2-hydroxybenzonitrile (39.25 g, 329 mmol) in dimethylformamide (39.25 g) was added. Potassium carbonate (63.5 g, 459 mmol) and DABCO (0.34 g, 3.03 mmol) were added subsequently. The mixture was heated to 80° C. for 75 min, then all dimethylformamide was removed by vacuum distillation. The semi-solid residue was cooled to 80° C., then toluene (168 g) was added, followed by water (160 mL). The mixture was stirred at 80° C. for 30 min, then the emulsion was poured into a 1 L separator funnel containing a further 160 mL hot water. The lower aqueous phase, and middle phase were separated off and the toluene phase was transferred to a 500 mL flask. The aqueous and middle phases were stirred at 80° C. with a further 20 mL toluene, and then the two phases separated. The combined toluene phases were evaporated in vacuo at 65° C. until a thick syrup remained (130.45 g). This was suspended in methanol (88 g, 110 mL) at 60° C. under a reflux condenser and stirred until homogeneous, then allowed to cool slowly to ambient temperature overnight under agitation. The slurry was further cooled to 2° C. over 30 min, then the slurry was filtered, and washed with cold methanol (2×10 mL). The solids were dried under vacuum affording 97.57 g azoxystrobin (98.4% pure, 79.4% yield).

Comparative Example 3

In a 500 mL flask equipped with a magnetic stirrer, (E)-methyl 2-(2-((6-chloropyrimidin-4-yl)oxy)phenyl)-3-methoxyacrylate (100 g, 97% pure, 302 mmol) was suspended in dimethylformamide (100 mL) at ambient temperature, and then 2-hydroxybenzonitrile (41 g, 341 mmol) and potassium carbonate (29.3 g, 212 mmol) were added. The mixture was placed on an oil bath at 120° C. The mixture was stirred at 120° C. for 3 h, then cooled to 80° C. and diluted with toluene (200 mL) and washed with water (250 mL) at that temperature. The upper organic portion was evaporated to dryness under vacuum at 60° C. This was dissolved in methanol (125 mL) at 55° C., allowed to cool freely to ambient temperature under agitation. The resulting slurry was cooled to 0° C. for 20 min, then the solids were recovered by suction filtration, washed with cold methanol (30 mL) and then dried under vacuum at ambient temperature, affording the product azoxystrobin (103.2 g, 97.7% pure, 82.6% yield) as a free flowing pale brown powder.

Comparative Example 4

In a 500 mL flask equipped with a magnetic stirrer, (E)-methyl 2-(2-((6-chloropyrimidin-4-yl)oxy)phenyl)-3-methoxyacrylate (100 g, 97% pure, 302 mmol) is suspended in dimethylsulfoxide (100 mL) and then 2-hydroxybenzonitrile (41 g, 341 mmol) and potassium carbonate (29.3 g, 212 mmol) were added. The mixture was placed on an oil bath at 100° C. The mixture was stirred at 100° C. for 3 h, under a mild vacuum to remove any generated water by distillation. The mixture was then cooled to 80° C. and diluted with toluene (150 mL) and washed with water (2×100 mL) at that temperature. The upper organic portion was evaporated to dryness under vacuum at 60° C. This was dissolved in methanol (125 mL) at 55° C., allowed to cool freely to ambient temperature under agitation, seeding with pure azoxystrobin (0.2 g) as appropriate. The resulting slurry was cooled to 0° C. for 20 min, then the solids were recovered by suction filtration, washed with cold methanol (30 mL) and then dried under vacuum at ambient temperature, affording the product azoxystrobin (101.1 g, 97.6% pure, 80.8% yield) as a free flowing pale brown powder.

The previous examples are summarized in table 1.

TABLE 1

|  | Product | Solvent | Catalyst | Reaction conditions | Yield |
| --- | --- | --- | --- | --- | --- |
| Example 1 | Azoxystrobin | water | N-methyl-piperidine | $K_2CO_3$, 100° C., 5 h | 91.2% |
| Example 2 | Azoxystrobin | water | N-methyl-piperidine | KOH, 100° C., 5 h | 86.6% |
| Example 3 | Azoxystrobin | water | 1-methyl-pyrrolidine | $K_2CO_3$, 120° C., 5 h | 88.1% |
| Example 4 | Azoxystrobin | water | DABCO | KOH, 120° C., 3 h | 96.5% |
| Example 5 | Azoxystrobin | water | N-methyl-piperidine | KOH, 120° C., 4½ h | 88% |
| Example 6 | DMA | water | DABCO | $K_2CO_3$, 100° C., 90 min | 95% |
| Example 7 | DMA | water | N-methyl-piperidine | $K_2CO_3$, 100° C., 5 h | 89% |
| Comparative example 1 | Azoxystrobin | water | No catalyst | $K_2CO_3$, 120° C., 22 h | 73% |
| Comparative example 2 | Azoxystrobin | DMF | DABCO | $K_2CO_3$, 80° C., 1.5 h | 79.4% |
| Comparative example 3 | Azoxystrobin | DMF | No catalyst | $K_2CO_3$, 100° C., 4 h | 82.6% |
| Comparative example 4 | Azoxystrobin | DMSO | No catalyst | $K_2CO_3$, 100° C., 3 h | 80.8% |

Example 9

A series of experiments were carried out based on the same reactions conditions and amounts as provided for in example 2 except for using different amounts of water as reaction medium comprising various amounts of toluene. The reactions were followed over time and conversion of starting materials followed using GC with internal standards. Results are provided in the table below:

TABLE 2

| | mass | Vol. | mass | w/w % toluene of reaction | Conversion | | | | |
| --- | --- | --- | --- | --- | --- | --- | --- | --- | --- |
| Entry | water | toluene | toluene | medium | 1 h | 2 h | 3 h | 4 h | 5 h |
| A | 30 | 0 | 0 | 0% | 64.2 | 86.7 | 92.7 | 99 | 99.4 |
| B | 30 | 3 | 2.6 | 8.0% | 58.9 | 90.7 | 94.6 | 98.2 | 99.4 |

TABLE 2-continued

| Entry | mass water | Vol. toluene | mass toluene | w/w % toluene of reaction medium | Conversion | | | | |
|---|---|---|---|---|---|---|---|---|---|
| | | | | | 1 h | 2 h | 3 h | 4 h | 5 h |
| C(c) | 30 | 12 | 10.4 | 25.8% | 48.3 | 66.4 | 81.7 | 93.9 | 91.6 |
| D(c) | 30 | 18 | 15.7 | 34.3% | 44.7 | 53.3 | 67.7 | 65.9 | 78.5 |
| E(c) | 30 | 30 | 26.1 | 46.5% | 39.6 | 46.3 | 53.4 | 56.6 | 68.8 |
| F | 45 | 0 | 0.0 | 0.0% | 57.0 | 76.5 | 81.3 | 92.1 | 97.2 |
| G | 45 | 4.5 | 3.9 | 8.0% | 54.0 | 70.2 | 90.4 | 90 | 95.7 |
| H(c) | 45 | 9 | 7.8 | 14.8% | 48.7 | 65.1 | 84.1 | 85.1 | 88.6 |
| I | 60 | 0 | 0 | 0% | 51.4 | 64.7 | 84.6 | 88.9 | 92.3 |
| J(c) | 60 | 12 | 10.4 | 14.8% | 41.6 | 58.2 | 69.6 | 72.6 | 82.9 | c = comparative

The crude yield of azoxystrobin for entry A, B, E, H, J was determined to be 94.5, 94.2, 76.9%, 74.7%, 79.7%, respectively.

The invention claimed is:

1. A process for preparing a compound of formula (I)

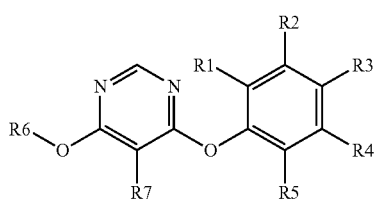
(I)

which comprises either:
a) reacting a compound of formula (II)

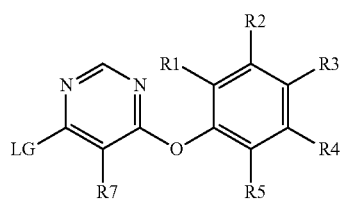
(II)

with an alcohol of the formula R6-OH, or a salt thereof,
i) in the presence of between 0.05 and 40 mol % of a tertiary-amine catalyst or combination of tertiary amine catalysts; and
ii) using water as reaction medium and wherein the reaction medium contains less than 10 w/w% of organic solvent ;
or
b) reacting a compound of formula (III)

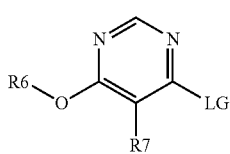
(III)

with a compound of formula (IV)

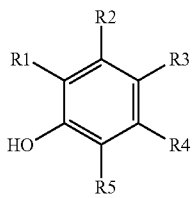
(IV)

or a salt thereof,
i) in the presence of between 0.05 and 40 mol % of a tertiary-amine catalyst or a combination of tertiary amine catalysts; and
ii) using water as reaction medium and wherein the reaction medium contains less than 10 w/w % of organic solvent ;
wherein:
LG represents a leaving group;
R1, R2, R3 and R4 represent, independently of one another, hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulphonyl;
R5 is hydrogen, halogen, cyano, nitro, alkylcarbonyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulponyl, or one of the following radicals:

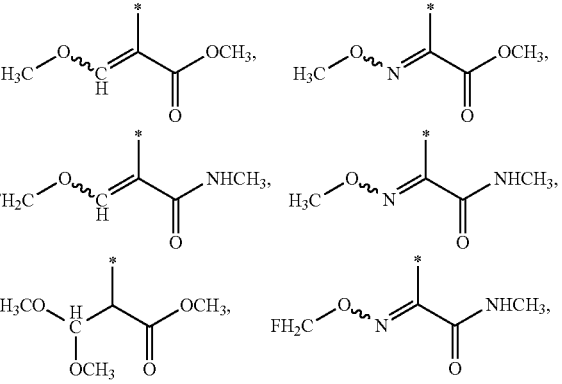

-continued

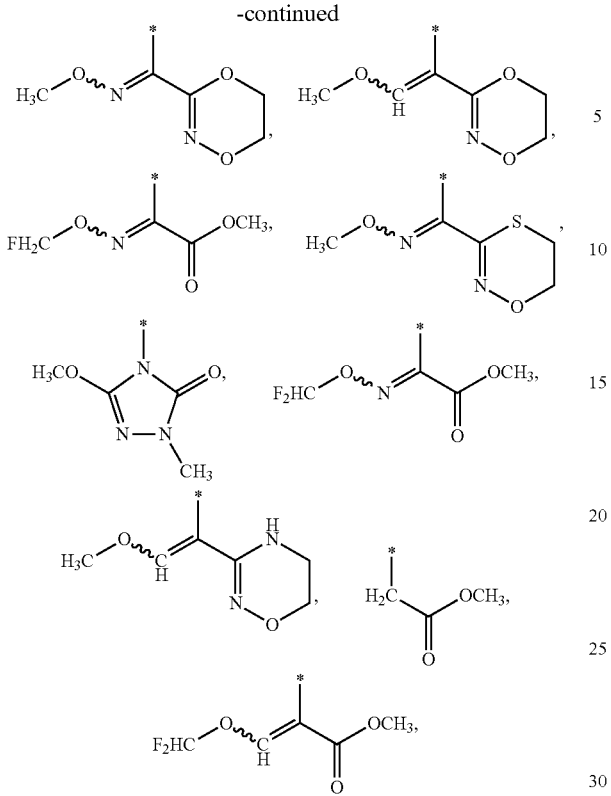

wherein * denotes the point of attachment to the phenyl radical of formula (I);
R6 is substituted or unsubstituted aryl, or substituted or unsubstituted heterocyclyl, or a salt thereof;
R7 is hydrogen, fluorine, chlorine or bromine;
with the proviso that R6 and the radical:

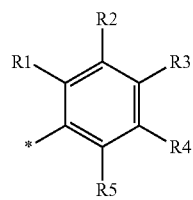

are different from each other.

2. The process according to claim 1, wherein the amount of water used as reaction medium is higher than 0.2:1 (w/w) of water:coupling-component.

3. The process according to claim 1, wherein the catalyst comprises a compound selected from:
a piperidine-based molecule of the formula (VI)

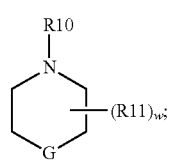

a 1,4-diazabicyclo[2.1.1]hexane-based molecule of the formula (VII)

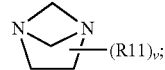

a pyrrolidine-based molecule of the formula (VIII)

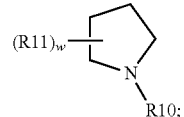

a tertiary amine-based molecule of the formula (IX)

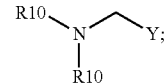

a azepine-based molecule of the formula (X)

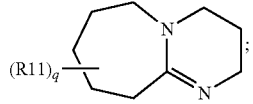

a Quinuclidine-based molecules of the formula (XI)

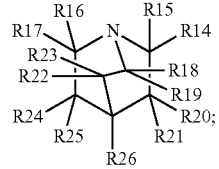

a hexamethylenetetramine of the formula (XII)

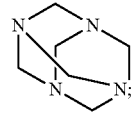

a triazole-based molecule of the formula (XIII)

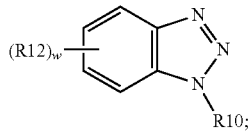

and
a 1,4-diazabicyclo[2.2.2]octane-based molecule of the formula (XIV)

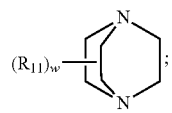

(XIV)

wherein:
q is 0, 1, 2, 3, 4 or 5;
v is 0, 1, 2 or 3;
w is 0, 1, 2, 3 or 4;
X is halogen;
Y is $CH_2N(CH_3)_2$, H, or C1-C4 alkyl;
G is C, S, O or N;
R10 represents, independently, straight or branched alkyl, substituted or unsubstituted benzyl, substituted or unsubstituted phenyl, halogen, cyano, hydroxyl, nitro, alkyl-carbonyl, allyl, formyl, alkoxycarbonyl, aminocarbonyl, alkylaminocarbonyl, dialkylaminocarbonyl, or optionally halogen-substituted alkyl, aryl, alkoxy, alkylthio, alkylsulphinyl or alkylsulphonyl;
R11 represents, independently, a substituted or unsubstituted carbon bridge of 1-3 carbon atoms, or represents independently straight or branched alkyl, substituted or unsubstituted benzyl, alkoxy, alcohol, alkenyl, carbonyl, or carboxylate;
R12 represents, independently, $N(CH_3)_2$, C3-C6 substituted or unsubstituted heterocyclyl, substituted or unsubstituted benzyl, substituted or unsubstituted phenyl, straight or branched alkyl, halogen, cyano, nitro, alkylcarbonyl, formyl, alkoxy-carbonyl, aminocarbonyl, alkylaminocarbonyl, dialkylaminocarbonyl, or represents optionally halogen-substituted alkyl, aryl, alkoxy, alkylthio, alkylsulphinyl or alkylsulphonyl;
R13 represents a straight or branched C1-C18 alkyl;
R14, R15, R16, R17, R18 and R19 represents, independently of one another, hydrogen, halogen, methyl, methoxy, methylene or cyano; or, independently, R14 and R15, R16 and R17, R18 and R19 together form =O, =S, —N or =C(R30)(R31), wherein R30 and R31 are, independently, hydrogen or R10;
R20, R21, R22, R23, R24 and R25 represents, independently of one another, hydrogen, halogen, alkenyl, alkynyl, alkylcarbonyl, formyl, alkoxycarbonyl, amino-carbonyl, alkylaminocarbonyl, dialkylaminocarbonyl, alkyl, aryl, alkoxy, alkylthio, alkylsulphinyl or alkylsulphonyl aryl groups, heterocyclyl, cycloalkyl, alkoxy, aryloxy, cycloalkyloxy, optionally substituted silyloxy, or, independently, R20 and R21, R22 and R23 and R24 and R25 together form =O, =S, =N or =C(R30)(R31), wherein R30 and R31 are, independently, hydrogen or R10;
R26 represents hydrogen, halogen, alkenyl, alkynyl, alkylcarbonyl, formyl, alkoxy-carbonyl, aminocarbonyl, alkylaminocarbonyl, dialkylaminocarbonyl, alkyl, aryl, alkoxy, alkylthio, alkylsulphinyl or alkylsulphonyl aryl groups, heterocyclyl, cyclo-alkyl, alkoxy, aryloxy, cycloalkyloxy or optionally substituted silyloxy.

4. The process according to claim 3, wherein the catalyst is chosen among one or more of the following compounds according to formulae VI to XIV:

compounds of the formula (VI) wherein w is 0, 1 or 2; G is either C or O; R10 is alkyl, preferably C1-C4, most preferably methyl; R11 is a substituted or unsubstituted carbon bridge of 1-3 carbon atoms, or is independently straight or branched C1-C4-alkyl, preferably 1 bridging carbon atom; or compounds of the formula (VII) wherein w is 0 or 1; R11 is a straight or branched alkyl, preferably C1-C4 straight or branched alkyl, and most preferably methyl; or compounds of the formula (VIII) wherein w is 0 or 1; R10 is straight or branched C1-C6 alkyl, allyl, or substituted or unsubstituted benzyl, preferably straight C1-C3 alkyl, allyl, unsubstituted benzyl, most preferably methyl, allyl or unsubstituted benzyl; R11 is a straight or branched alkyl, carbonyl, or alkenyl, preferably C1-C4 straight or branched alkyl, and most preferably methyl; or compounds of the formula (IX) wherein R10 is C1-C8 straight or branched alkyl, preferably C1-C4 straight or branched alkyl, and most preferably methyl or ethyl; Y is $CH_2N(CH_3)_2$, H, or C1-C4 alkyl, preferably $CH_2N(CH_3)_2$, H or methyl and most preferably $CH_2N(CH_3)_2$, or H; or compounds of the formula (X) wherein q is 0 or 1; R11 is C1-C4 alkyl, preferably methyl or ethyl, and most preferably methyl; or compounds of the formula (XI) wherein the compound is quinuclidine, 3-quinuclidinol or 3-quinuclidinone, or an acid salt thereof; or the compound of formula (XII) is hexamethylenetetramine; or compounds of the formula (XIII) wherein w is 0 or 1; R10 is hydroxyl, alkoxy or C1-C4 alkyl, preferably hydroxyl, methoxy, or methyl and most preferably hydroxyl; R12 is halogen, cyano, nitro, alkoxy, C1-C4 alkyl, preferably halogen, cyano, nitro, or methyl; or compounds of the formula (XIV) wherein w is 0, 1, or 2; R11 is a straight or branched alkyl, preferably C1-C4 straight or branched alkyl, and more preferably methyl.

5. The process according to claim 4, wherein the catalyst comprises 1,4-diazabicyclo[2.2.2]octane (DABCO), N-methyl-pyrrolidine, N-methylpiperidine, N-methylmorpholine, hexamethylenetetramine, 1,4-diazabicyclo[2.1.1]hexane, quinuclidine, 3-quinuclidinol, or 3-quinuclidinone.

6. The process according to claim 1, wherein R1, R2, R3 and R4 are, independently, hydrogen, fluorine, chlorine, bromine, cyano, nitro, acetyl, propionyl, methoxycarbonyl, ethoxycarbonyl, aminocarbonyl, methylaminocarbonyl, ethyl-aminocarbonyl, dimethylaminocarbonyl, diethylaminocarbonyl, methyl, ethyl, n- or i-propyl, n-, i-, s- or t-butyl, methoxy, ethoxy, n- or i-propoxy, methylthio, ethylthio, methylsulphinyl, ethylsulphinyl, methylsulphonyl, ethylsulphonyl, trifluoromethyl, trifluoroethyl, difluoromethoxy, trifluoromethoxy, difluorochloromethoxy, trifluoro-ethoxy, difluoromethylthio, difluorochloromethylthio, trifluoromethylthio, trifluoro-methylsulphinyl, or trifluoromethylsulphonyl.

7. The process according to claim 6, wherein R1, R2, R3 and R4 are, independently, hydrogen or methyl.

8. The process according to claim 6, wherein R1, R2, R3 and R4 are each hydrogen.

9. The process according to claim 1, wherein R5 represents one of the following radicals:

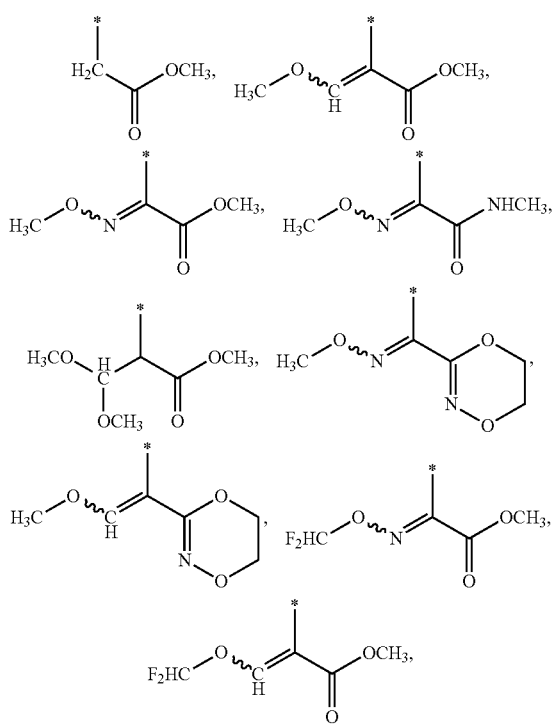

or a mixture thereof, where * denotes the point of attachment to the phenyl radical.

10. The process according to claim 9, wherein R5 is

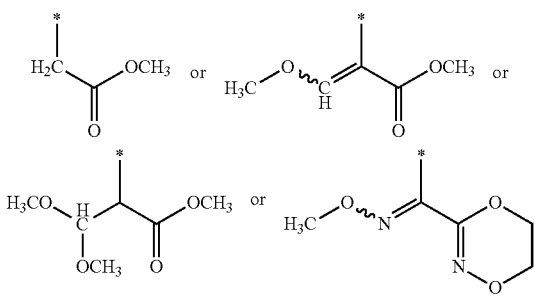

or a mixture thereof, where * denotes the point of attachment to the phenyl radical.

11. The process according to claim 1, wherein R6 represents one of the following:

a heterocycle having 3 to 7 ring members, optionally substituted by halogen or by C1-6 alkyl, C1-6 alkoxy, C1-6 halogenoalkyl or C1-6 halogenoalkoxy; or phenyl or naphthyl, each of which is optionally mono- to pentasubstituted by identical or different substituents selected from the group consisting of:

a. halogen, cyano, formyl or acetal protected formyl (for example the dimethyl or diethyl acetal, 1,3-dioxolan-2-yl, 1,3-dioxan-2-yl) carboxyl, carbamoyl, thiocarbamoyl, aminocarbonyl;

b. C1-8, straight-chain or branched, alkyl, oxyalkyl, alkoxy, alkoxyalkyl, alkyl-thioalkyl, dialkoxyalkyl, alkylthio, alkylsuphinyl or alkylsulphonyl having in each case 1 to 8 carbon atoms;

c. C2-6, straight-chain or branched, alkenyl or alkenyloxy;

d. C1-6, straight-chain or branched, halogenoalkyl, halogenoalkoxy, halogeno-alkylthio, halogenoalkyl-sulphinyl or halogenoalkylsulphonyl with between 1 and 13 identical or different halogen atoms;

e. C2-6, straight chain or branched, halogenoalkenyl or halogenoalkenyloxy with between 1 and 11 identical or different halogen atoms;

f. C1-6, straight-chain or branched, dialkylamino, alkylcarbonyl, alkylcarbonyl-oxy, alkoxycarbonyl, alkylaminocarbonyl, dialkylaminocarbonyl, arylalkylaminocarbonyl, dialkylaminocarbonyloxy, alkenylcarbonyl or alkynyl-carbonyl;

g. C3-6 cycloalkyl or cycloalkyloxy;

h. doubly attached C3-4 alkylene, C2-3 oxyalkylene or C1-2 dioxyalkylene, each of which is optionally mono- to tetrasubstituted by identical or different substituents selected from the group consisting of fluorine, chlorine, oxo, methyl, trifluoromethyl and ethyl; and i. the radical

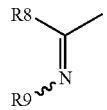

in which:

R8 is hydrogen, hydroxyl, C1-4 alkyl or C1-6 cycloalkyl; and

R9 represents hydroxyl, methoxy, ethoxy, amino, methylamino, phenyl or benzyl; or represents C1-4 alkyl or alkoxy, optionally substituted with cyano-, alkoxy-, alkylthio-, alkylamino-, dial kylamino- or phenyl; or represents C2-4 alkenyloxy or al kynyloxy; or represents benzoyl, benzoylethenyl, cinnamoyl, heterocyclyl; or represents phenylalkyl, phenylalkyloxy or heterocyclylalkyl, having in each case 1 to 3 carbon atoms in the alkyl moieties and being in each case optionally mono- to tri-substituted in the ring moiety by halogen and/or straight-chain or branched C1-4 alkyl or alkoxy.

12. The process according to claim 11, wherein R6 is optionally mono- to penta-substituted phenyl where the substituents are selected from halogen, cyano, formyl or acetal protected formyl, methoxycarbonyl, ethoxycarbonyl, aminocarbonyl, methylaminocarbonyl, ethylaminocarbonyl, dimethylaminocarbonyl, diethylamino-carbonyl, in each case straight-chain or branched C1-4 alkyl or halogenoalkyl or represents the radical:

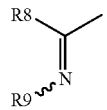

wherein R8 is hydrogen and R9 is hydroxyl, methoxy or ethoxy.

13. The process according to claim 12, wherein R6 is 2-cyanophenyl.

14. The process according to claim 1, wherein R7 is hydrogen, fluorine or chlorine.

15. The process according to claim 1, wherein the amount of catalyst is between 0.1 and 20 mol %.

16. The process according to claim 1 for preparing the compound of formula (Ia)

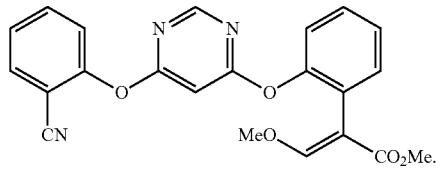
(Ia)

17. The process according to claim 1 for preparing the compound of formula (Ib)

(Ib)

18. The process according to claim 1 for preparing the compound of formula (Id)

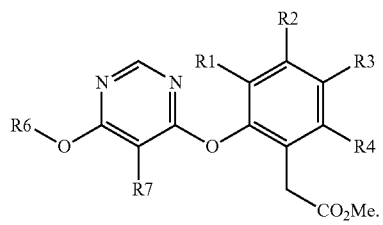
(Id)

19. The process according to claim 18, wherein the compound of formula (Id) is further subjected to a formylation step followed by a methylation step to obtain the compound of formula (If)

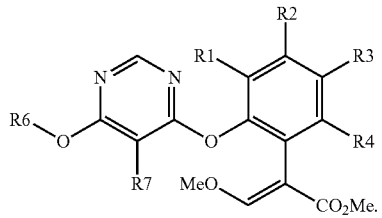
(If)

20. The process according to claim 19, wherein the process comprises the following reaction sequence

(Ib) Formylation →

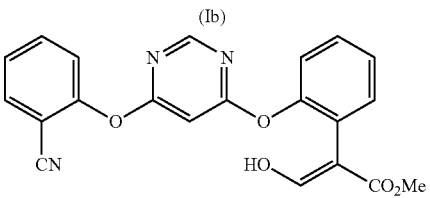
(Ib) Methylation →

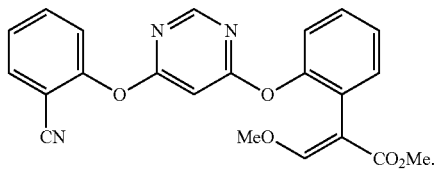
(Ia)

* * * * *